United States Patent [19]

Ahlin

[11] Patent Number: 4,568,280

[45] Date of Patent: Feb. 4, 1986

[54] CRANIOMANDIBULAR APPLIANCE

[76] Inventor: Jeffrey H. Ahlin, 1 Essex Ave., Gloucester, Mass. 01930

[21] Appl. No.: 503,449

[22] Filed: Jun. 13, 1983

[51] Int. Cl.⁴ .............................................. A61C 3/00
[52] U.S. Cl. ..................................... 433/6; 128/76 R
[58] Field of Search .................. 433/6, 24; 128/76 R, 128/136

[56] References Cited

U.S. PATENT DOCUMENTS

| | | | |
|---|---|---|---|
| 3,224,441 | 12/1965 | Monaghan | 128/136 |
| 3,319,626 | 5/1967 | Lindsay | 128/136 |
| 3,478,742 | 11/1969 | Bohlmann | 433/6 |
| 3,898,736 | 8/1975 | Bergersen | 433/6 |
| 4,211,008 | 7/1980 | Lerman | 433/6 |
| 4,371,336 | 2/1983 | Hilleman | 433/6 |

FOREIGN PATENT DOCUMENTS 2320501  11/1974  Fed. Rep. of Germany .... 128/76 R

Primary Examiner—John J. Wilson
Attorney, Agent, or Firm—Cesari and McKenna

[57] ABSTRACT

A craniomandibular appliance for treating mandibular retrogranathism and craniomandibular disorders comprising a unitary insert of a remoldable thermoplastic in the form of a dental arch defined by inner and outer walls and an interconnecting web to form channels for receiving the dental arches. The web establishes a defined separation between the occlusal surfaces of the upper and lower teeth and positions the mandible in a more forward position to obtain a reduced click or non-click condylar position.

13 Claims, 10 Drawing Figures

CRANIOMANDIBULAR APPLIANCE

BACKGROUND OF THE INVENTION

A. Field of the Invention

The invention relates to pathologic conditions known as temporomandibular joint disorders and to a method and apparatus for treating them.

B. Prior Art

Temporomandibular joint disorders ("TMJ disorders") are pathologic conditions of the craniomandibular articulation which affect mandibular opening, mastication, and deglutition. A common type is internal derangement. Mild internal derangement of the TMJ may manifest itself as a "clicking" or "popping" of the disc within the joint. More severe symptoms include headache, neck pain, back pain or facial pain. Stooping and altered head and body posture may be additional signs of disorder of the craniomanidibular articulation. The problem is widespread: It has been estimated that up to 50% of the population seeking dental treatment exhibits some degree of TMJ dysfunction. The nature of the disorder is described more fully in an article by myself and by F. J. Ramos-Gomez entitled "Treatment of Temporomandibular Joint Related Headaches In the Pedodontic Patient: A Preliminary Report" appearing in the *Journal of Pedodontics*, Vol. 6, No. 2 (Winter 1982.).

One method of treatment for craniomandibular disorder (internal derangement) includes repositioning the mandible, usually in a more forward and opened position. Typically, this is accomplished by means of an appliance which is attached to the upper or lower teeth or by a "European style" appliance for maintaining a preset mandibular position. Such appliances typically comprise a number of "pads" (usually of hard, acrylic plastic) fitted to selected teeth and joined by structural wires which reposition the mandible. Screw-type adjustments are usually provided in the appliance to accomodate changes in the user's condition. These appliances may be cosmetically unattractive or sore to the gingival tissues, and have served as a barrier to treatment by some who could benefit from it. Further, they are time consuming to fabricate and adjust, and may be uncomfortable or cumbersome for the patent. A survey of the development and construction of some typical maxillofacial appliances is set forth in an article entitled "The Historical Development of Maxillofacial Orthopedic Techniques" authored by the applicant and appearing in *The Bulletin Of The History of Dentistry*, Vol. 30, No. 2, Oct. 1982.

Careful fitting and fabrication of the appliances is also a requisite to successful treatment. Typically, the fabrication is done in dental laboratories by skilled technicians who operate from a casting made by the clinician who is treating the patient. The fabrication is expensive, and the requisite technical laboratory skills are frequently lacking in many countries. In many areas of the world, therefore, a significant portion of the population is barred from access to the effective treatment of craniomandibular disorders.

BRIEF DESCRIPTION OF THE INVENTION

A. Summary of the Invention

Treatment of patients with TMJ disorders over a period of years has led me to conclude that a less expensive and more comfortable approach to treatment is required. In particular, I have determined that some TMJ disorders can be treated effectively with a minimum of discomfort with the assistance of a unitary remoldable maxillofacial orthopedic appliance that has neither wires nor pads and that is fitted directly to the patient by the clinician without further laboratory work. The appliance is similar in some respects to those mouthpieces worn by athletes to protect the teeth against injury, or to devices used by orthodontists to correct tooth positioning. Unlike those devices and mouthpieces, however, the appliance described herein neither repositions the teeth as in conventional orthodontia, nor guards them from shock as in athletic mouthpieces. Rather, it operates on the patient's mandible by repositioning it in a more forward and downward position to thereby obtain a reduced click or non-click condylar position.

Specifically, the appliance of the present invention comprises a remoldable insert having inner and outer generally vertical walls transversely interconnected at approximately their mid sections by a generally horizontal web and forming, with the walls, upper and lower channels for receiving therein the upper and lower dental arches, respectively.

In the preferred form of the appliance, a plurality of ribs are formed on the upper and lower surfaces of the web; the ribs extend transversely between the walls and are spaced on the order of 5 millimeters apart. The ribs on the respective surfaces are preferably intercalated with respect to each other. This structure provides the desired strength and spacing, but minimizes the surface area of contact between the teeth and web and thus minimizes the suction and friction forces that might otherwise result when the appliance is removed. Further, it minimizes the web mass otherwise required for spacing and facilitates manufacture by reducing shrinkage in the web region on cooling; this greatly accelerates the molding process. Thus, both physiological and manufacturing ends are served by the ribbed structure.

The ribs receive the occlusal surfaces of the maxillary and mandibular arches, respectively, and space the teeth by a defined amount to thereby move the condylar head downwardly. Further, at least the medial portion of the lower channel is preferably positioned somewhat outwardly of the upper channel to thereby assist in positioning the mandible forewardly. The requisite offset between the two channels is small; an offset of 1–2 millimeters should suffice in most cases. Precise adjustment of the mandibular position is made by the clinician as described below.

The height of the outer wall increases slightly in the rearward (posterior) direction and is somewhat diminished in the medial portion to accomodate the buccinator muscles. The height of the outer wall is generally less than that of the inner wall in most regions; it has a medial portion of diminished height in a region approximately extending from the canine teeth; intermediate lateral portions of maximum height in the vicinity of the canine teeth; and anterior lateral portions of decreasing height (i.e., tapered) posteriorly of the incisors.

The appliance is formed of a remoldable material, preferably a thermoplastic material such as an ethylene vinyl acetate material manufactured by the Dupont Corporation and sold under the tradename "Elvax" resin. This material has the desirable property that it softens to a moldable form when heated to the temperature of boiling water, but reverts to a pliant yet firm form on cooling. Thus, it can be molded in situ (i.e., in the patient's mouth) to confirm to the desired position of the mandible (and therefore the condylar head). It is relatively physiologically inert and not attacked by mouth acid. It is tough and thus nearly impossible to chew through, yet remains flexible in the mouth.

In addition to providing positive therapeutic treatment, the appliance of the present invention may also be used to aid the clinician in a differential diagnosis. Further, it provides a simple and more objective means of confirming a clinical impression of craniomandibular disorder, while minimizing the need to rely on invasive radiographic techniques like arthrography. It thus limits or reduces radiation to the patient from radiographic techniques such as lateral skull, panographic, transcranial, polycycloidal tomography, or CAT scan procedures which may otherwise by necessary to aid in diagnosis of craniomandibular disorders. Any reduction of even low ionizing radiation is beneficial, especially for young, rapidly growing patients.

B. Objects of the Invention

Accordingly, it is an object of the invention to provide a method and apparatus for treatment of temporomandibular joint disorders (internal derangement).

Further, it is an object of the invention to provide a method and apparatus for treatment of temporomandibular joint disorders and which significantly minimizes patient discomfort.

Further, it is an object of the invention to provide a method and apparatus for treatment of temporomandibular joint disorders and which is cosmetically improved with respect to present methods and apparatus, yet markedly less expensive.

Yet another object of the invention is to provide a method and apparatus for treatment of temporomandibular joint disorder which simplifies mandibular repositioning.

Further, it is an object of the invention to provide a method and apparatus for aid in the treatment of Class II malocclusion and retrognathia.

DETAILED DESCRIPTION OF THE INVENTION

The foregoing and other and further objects and features of the invention will be more readily understood on reference to the following detailed description of the invention, when taken in conjunction with the accompanying drawings, in which.

Figure 1:
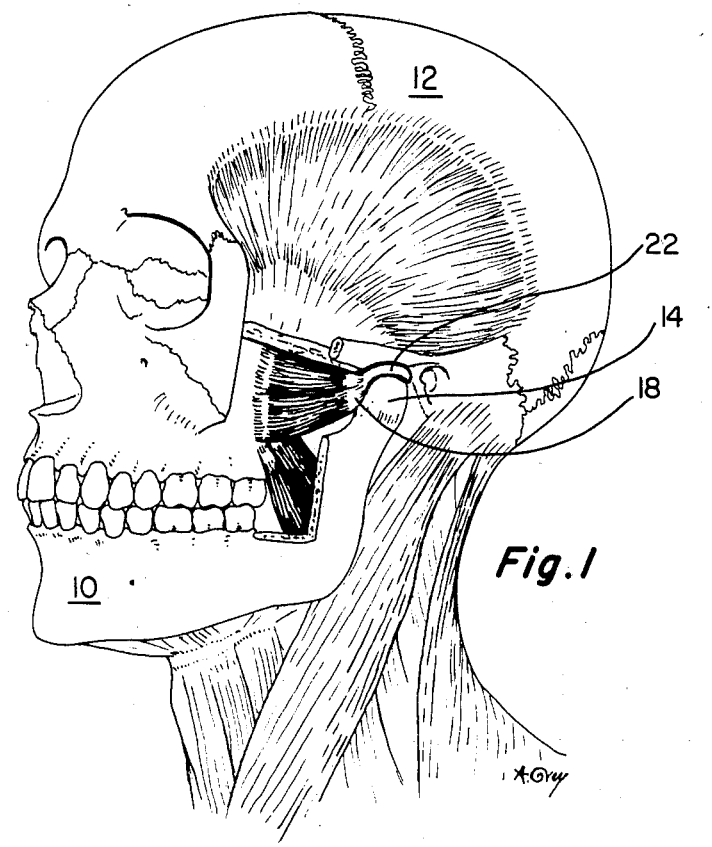
FIG. 1 is a sketch of a skull and certain of the bone and muscle structure of consequence with respect to the present invention.

In FIG. 1, the mandible 10 of a skull 12 has a condylar head 14 that articulates with the temporal bone 16. Lateral pterygoyd muscle 18 has a posterior attachment connecting it to the condylar neck and articular disc 22 extending between the condylar head and the temporal bone. In the case of internal derangement of TMJ disorder, the position of the condylar head is displaced (generally superiorly and distally) to such an extent that the articular disc is displaced from its normal position. This not only affects the pterygoid muscle but may also interfere with the ability to move the mandible in a normal fashion. In addition to the discomfort this may cause in connection with talking, eating, and other activities, it may also impose a strain on the muscles associated with the mandible. This strain or resulting spasm may be severe enough as to cause patient discomfort or even significant physical impairment.

Figure 3:
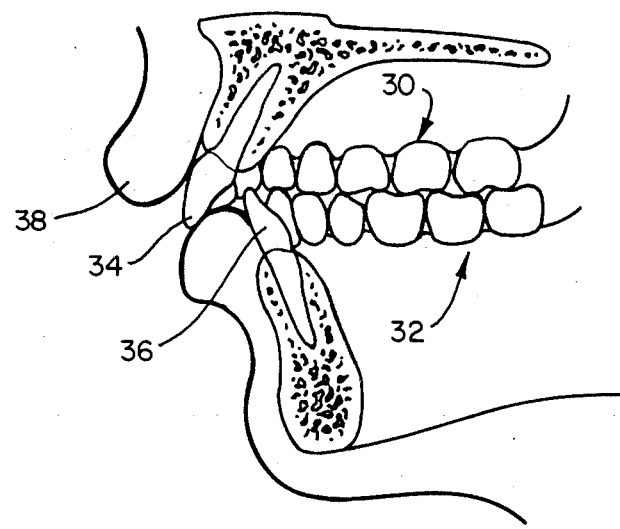
FIG. 3 is a partial medial sectional view of the maxillary and mandibular structure of a patient exhibiting retrognathia.

Turning now to FIG. 3, an enlarged medial sectional view of the anterior portion of the mandibular and maxillary structure of a patient exhibiting retrognathia is shown. The teeth of the upper dental arch 30 and the lower dental arch 32 closely abut each other and the incisor teeth 34 of the upper dental arch overhang the incisor teeth 36 of the lower dental arch. This position of the mandible may interfere with proper function of the mandible, and may strain the muscles associated with it, as noted previously, but also may cosmetically mar the patient. Thus, in FIG. 3 it will be noted that the lower lip is everted (turned outwardly) with respect to the upper lip.

Figure 2:
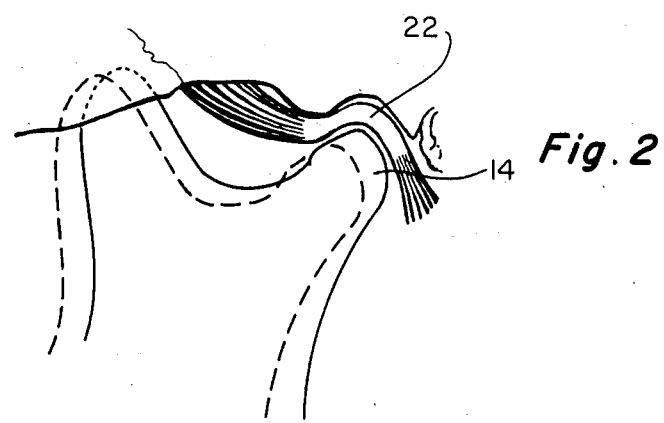
FIG. 2 is an enlarged sketch of the condylar head region.
Figure 4:
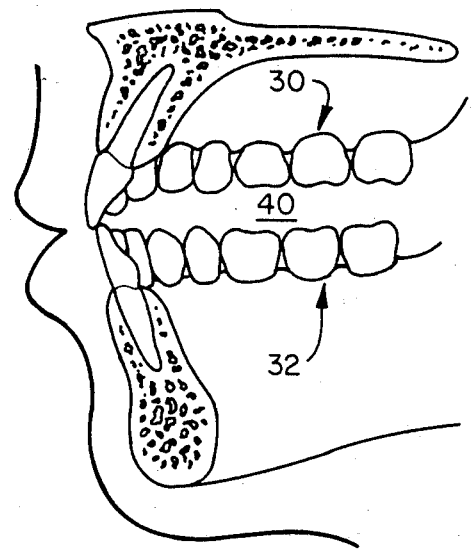
FIG. 4 is a partial medial sectional view of the maxillary and mandibular structure showing the desired mandibular repositioning.
Figure 5:
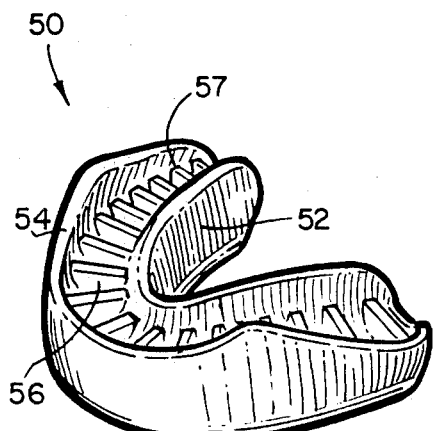
FIG. 5 is a view in perspective of an appliance in accordance with the present invention which effectuates the positioning shown in FIG. 4.

FIG. 4 shows the desired positioning of the mandible. As there illustrated, the upper and lower dental arches 30, 32, respectively are separated by a slight gap 40 (of the order of 3-6 millimeters), and the upper and lower incisor teeth 34, 36, respectively generally abut each other near their incisal edges. From this position, the condylar head of the mandible is moved downward and forward to the position illustrated by the chain lines in FIG. 2, thereby relieving strain on the articular disc and muscles associated with the mandible, and increasing functional mobility of the mandible. Further, it repositions the upper and lower lips opposite each other, and significantly improves the cosmetic appearance of the patient.

The orthopedic appliance for accomplishing the desired mandibular repositioning is illustrated in detail in FIGS. 5 through 10. The appliance 50 has inner and outer walls 52, 54, respectively, interconnected by a horizontal web 56 having ribs 58, 60 (FIG. 8) on the upper and lower surfaces thereof, respectively. The walls 52, 54 and web 56 form upper and lower channels 57, 59 respectively for receiving the upper and lower dental arches of a patient. As may be seen most clearly from FIG. 8, the ribs 58, 60 are intercalated with respect to each other, that is, as viewed in a vertical direction, the ribs 58 are positioned intermediate the ribs 60. The ribs are separated from each other by a distance of approximately 5 millimeters, and are approximately each 1.5 millimeter in height. The thickness of the web 56 is approximately 1.8 millimeters.

The ribs 58, 60, together with the web 56, establish the requisite vertical spacing illustrated in FIG. 4. Further, they limit the extent to which the teeth are imbedded in the appliance and form air pockets when the appliance is molded into its final position as described more fully below, so as to limit the suction that might otherwise develop when the appliance is removed. In addition to these physiologic functions, the ribs also serve the purpose of minimizing the mass of material that must be used in the web 56 to maintain the desired spacing. As a result, the time required to form the appliance is reduced, and thus the rate at which it can be manufactured is significantly increased. Further, the shrinkage which would normally occur were the web 56 a solid mass of the requisite total thickness without ribs is minimized or entirely eliminated, and thus manufacturing defects are essentially eliminated.

Figure 6:
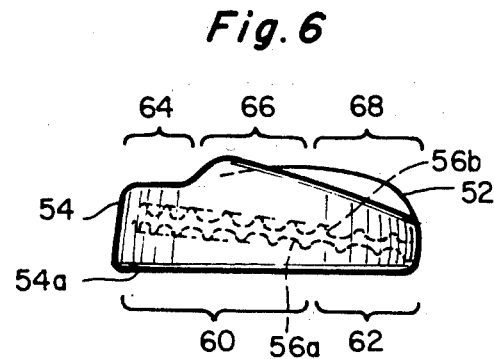
FIG. 6 is a side elevationalr view of the appliance.
Figure 8:
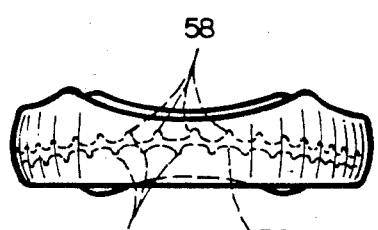
FIG. 8 is a front elevational view of the appliance with portions broken away to illustrate constructional details.
Figure 7:
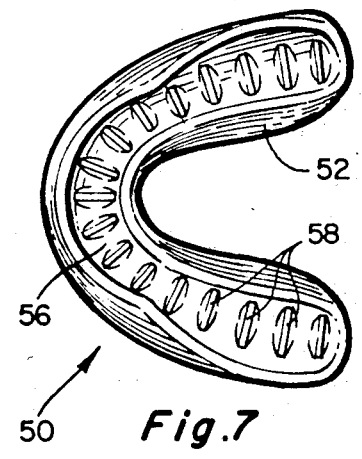
FIG. 7 is a plan sectional view of the appliance.
Figure 9:
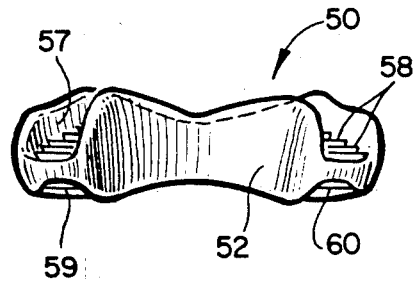
FIG. 9 is a rear elevational view of the appliance.
Figure 10:
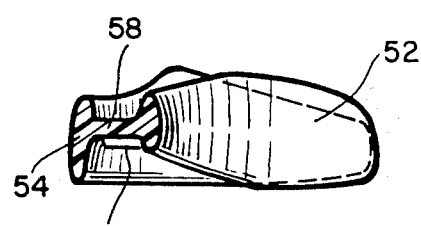
FIG. 10 is a side sectional view along the lines 10—10 of FIG. 7.

As may be seen more clearly from FIGS. 6 and 8, the bottom portion 54a of the outer wall 54 has essentially a constant height with respect to the lower face 56a of the web 56 in the anterior medial and forward lateral region 60, and a slight upward taper in the posterior lateral region 62. The region 62 corresponds approximately to the region of the molar teeth. Conversely, the upper segment 54b of the outer wall 54 has a region 64 of reduced height in the anterior medial region (extending approximately in the region between, and including, the canine teeth) an elevated portion in the region 66 extending over approximately the bicuspid teeth, and a sharply tapered region 68 extending to the posterior of the appliance. The region 64 provides room for breathing through the teeth in that region, and also minimizes the surface area in contact with the teeth and thus the forces which may be applied to the teeth. Additionally, it greatly enhances the cosmetic attractiveness of the appliance. The elevated portion in region 66 distributes the retaining forces onto the canine teeth and thus further alleviates the forces on the incisors which might otherwise tend to shift the teeth posteriorly. Finally, the tapered region 68 minimizes the mass of the appliance by eliminating the material in regions where the retaining force is minimal. The comfort of the user is thereby significantly promoted.

In similar manner the inner wall 52 has upper and lower wall portions 52a, 52b, respectively, of relatively constant height with respect to the web 56 throughout most of their extent, but of slightly reduced height in both the upper and lower wall sections in interior medial sections 70, 72, respectively.

In use, the appliance of FIGS. 5 through 10 preferably is supplied in a variety of sizes to accomodate mouths of differing sizes. The appliance is used by heating it, e.g., by immersion in water above 200° F., for a time sufficient to soften it to a pliable state, and thereafter inserting it into the patient's mouth with the upper and lower dental arches positioned within the channels 57, 59, respectively. The clinician then adjusts the position of the mandible of the patient to a position corresponding generally to that of FIG. 4, that is, with the mandible such that there is a slight gap 40 between the upper and lower dental arches, and with the incisal surfaces of the incisors butting against each other. The clincian and the patient then set the appliance in a position which will hold the requisite mandibular position. This is accomplished by the patient's pressing the rear wall 52 of the appliance against the back surfaces of the teeth with his or her tongue, while the clinician presses the front wall 54 against the front surfaces of the teeth. During this process, it is neither necessary nor desirable that the appliance be molded to the shape of the individual teeth, since the function of the appliance is not to fix the position of the teeth but rather to establish and fix the position of the mandible.

CONCLUSION

From the foregoing it will be seen that I have provided an improved crandiomandibular appliance for treating mandibular retrogranathism and craniomandibular disorders. The appliance dispenses completely with the acrylic pad and wire construction heretofore previously utilized and, instead, utilizes a remoldable insert which can be formed to shape within the patient's mouth to hold the mandible in a predetermined position. As treatment progresses, the same appliance can be reheated and reformed to a new shape as needed. The appliance completely dispenses with the need for laboratory construction, and thus enables clinicians in regions not having suitable laboratory facilities to provide the same level of treatment for craniomandibular disorders as is provided in regions having such facilities. The appliance is of significantly reduced cost to manufacture, since it is readily molded as an integral unit by conventional plastic molding techniques. The design is such that the upper and lower dental arches are held in a spaced-apart position of desired dimensions without the use of a massive web between the teeth. The construction also facilitates ready removal of the appliance for purposes such as eating, etc., without discomfort caused by suction effects.

Having illustrated and described my invention, I claim:

1. A craniomandibular appliance for treating mandibular retrognathism and craniomanidbular disorders, comprising a unitary insert of a thermoplastic material in the form of a dental arch having inner and outer generally vertical walls spaced apart from each other and connected by a generally horizontal ribbed web defined independently of a patient's teeth to form upper and lower channels for receiving the upper and lower dental arches, respectively, of a patient's mouth and moldable within said mouth to a fixed configuration establishing a desired mandibular position, said ribs having a top surface for contacting the occlusal surfaces of the teeth such that said ribbed web establishes a defined separation between the occlusal surfaces at the upper and lower teeth when said teeth are positioned therein.

2. A craniomandibular appliance according to claim 1 in which the inner wall portion of said lower channel extends anteriorly of the inner wall portion of said upper channel to thereby position the mandible anteriorly of the maxillary bone.

3. A craniomandibular appliance according to claim 2 in which the ribs on the upper and lower web are intercalated with respect to each other.

4. A craniomandibular appliance according to claim 3 in which said ribs are spaced on the order of 5 millimeters apart.

5. A craniomandibular appliance according to claim 1 in which the inner wall is of reduced height medially.

6. A craniomandibular appliance according to claim 1 in which the inner wall tapers posteriorly in the medial regions thereof.

7. A method of treating craniomandibular disorders, comprising the steps of:
   A. heating a remoldable insert to a plastic state,
   B. adjusting the insert to a first dental arch of the patient,
   C. repositioning the mandible of the patient into the desired position for treatment, D. closing the mouth of the patient to fix the other dental arch firmly into the insert, E. firmly pressing the insert against the dental arches of the patient to thereby fix the insert in a position corresponding to the desired mandible postition, and F. maintaining the mandibular positioning until the insert has set to thereby fix the mandible in the desired position.

8. The method of claim 7 in which said insert exposes at least the maxillary incisor teeth of the patient and covers at least the maxillary bicuspid teeth.

9. The method of claim 7 in which said insert comprises a remoldable plastic insert in the shape of an arch and moldable in response to finger and tongue pressure to conform generally to the dental arches of the patient to hold the mandible in a position of gentle stress anteriorly of its customary unstressed position.

10. The method of claim 9 in which said insert comprises an arch-shaped thermoplastic insert having a generally flat platform separating the upper and lower dental arches of the patient and vertically-extending walls defining, in cooperation with said platform, a lower, generally continuous channel for receiving the mandibular teeth therein and an upper discontinous channel
   for receiving the maxillary teeth therein and confining the maxillary teeth primarily in the regions anterior to the incisor teeth.

11. A craniomandibular appliance for treating retrognathism and craniomandibular disorders, comprising an insert in the shape of a dental arch and having inner and outer spaced, vertically extending walls defining a first generally continuous channel on one face thereof for receiving a first dental arch therein and defining a second discontinuous channel having first and second channel segments formed laterally and anteriorly on a second face thereof for receiving portions of a second dental arch therein, said insert formed of a thermoplastic material heatable to a pliable state exteriorly of a patient's mouth and moldable within said mouth, immediately after heating, to a fixed configuration establishing a desired mandibular position.

12. A craniomandibular appliance according to claim 11 in which the medial position of said second channel comprises a generally flat, wall-free channel bed substantially exposing the maxillary incisor teeth.

13. A craniomandibular appliance according to claim 11 in which said channel segments extend posteriorly of the maxillary incisor teeth.

* * * * *